(12) United States Patent
Nemeth et al.

(10) Patent No.: US 6,288,281 B1
(45) Date of Patent: Sep. 11, 2001

(54) DIRECT CARBONYLATION OF PARAFFINS USING AN IONIC LIQUID CATALYST

(75) Inventors: Laszlo T. Nemeth, Palatine; Jeffery C. Bricker, Buffalo Grove; Jennifer S. Holmgren, Bloomingdale; Lyle E. Monson, Rolling Meadows, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/714,704

(22) Filed: Nov. 16, 2000

(51) Int. Cl.$^7$ .................................................... C07C 45/49
(52) U.S. Cl. ..................... 568/342; 568/350; 568/351; 568/387; 568/393; 568/396; 568/401
(58) Field of Search ..................................... 568/342, 350, 568/351, 387, 393, 396, 401

(56) References Cited

U.S. PATENT DOCUMENTS

| | | | |
|---|---|---|---|
| 1,801,350 | * | 4/1931 | Hopff . |
| 2,346,701 | | 4/1944 | Pines et al. ............................ 260/488 |
| 2,874,186 | | 2/1959 | Friedman et al. ..................... 260/514 |
| 3,356,720 | | 12/1967 | Mirviss et al. ........................ 260/533 |
| 4,554,383 | | 11/1985 | Knifton ................................ 568/428 |

FOREIGN PATENT DOCUMENTS

| | | |
|---|---|---|
| WO 95/21806 | 8/1995 | (WO) . |
| WO 98/50336 | 11/1998 | (WO) . |
| WO 00/15594 | 3/2000 | (WO) . |

OTHER PUBLICATIONS

"Designer Solvents" by Michael Freemantle, *Chemical Engineering News*, Mar. 30, 1998, pp 32–37.

"Ionic Liquids for Clean Technology: An Update" by K.R. Seddon, *Molten Salt Forum*, vol. 5–6, 1998, pp. 53–62.

* cited by examiner

*Primary Examiner*—Sreeni Padmanabhan
*Assistant Examiner*—Sikarl A. Witherspoon
(74) *Attorney, Agent, or Firm*—John G. Tolomei; Frank S. Molinaro

(57) ABSTRACT

A process for the carbonylation of saturated hydrocarbons to give an oxygenated saturated hydrocarbon is disclosed and claimed. The process involves using an acidic ionic liquid catalyst to catalyze the carbon monoxide addition to the saturated hydrocarbon at reaction conditions to form an oxygenate. The acidic ionic liquid comprises a Lewis or Bronsted acid in combination with a quaternary nitrogen-containing compound. A specific example is a mixture of aluminum chloride and n-butylpyridinium chloride.

23 Claims, No Drawings

US 6,288,281 B1

DIRECT CARBONYLATION OF PARAFFINS USING AN IONIC LIQUID CATALYST

FIELD OF THE INVENTION

This invention relates to a process for the carbonylation of a saturated hydrocarbon to give an oxygenated saturated hydrocarbon. The process involves using an acidic ionic liquid catalyst such as a mixture of aluminum chloride and quaternary nitrogen-containing salts to catalyze the carbon monoxide addition to the saturated hydrocarbon at reaction conditions to form oxygenates.

BACKGROUND OF THE INVENTION

Liquid superacids, e.g., $HF/BF_3$, are use to catalyze reactions such as the alkylation of paraffins and the carbonylation of aliphatic hydrocarbons, see, WO 98/50336. However, the use of liquid super acids such as $HF/BF_3$ are not environmentally friendly and thus their replacement has received considerable attention. In the search for such replacement a family of compounds, known as ionic liquids, is receiving attention because they can act as both catalysts and solvents and have no measurable vapor pressure.

Ionic liquids are sometimes referred to as molten salts, but they are not molten salts in the sense of molten sodium chloride. Ionic liquids have melting points below room temperature and have liquid ranges of as much as 300° C. compared to the 100° C. liquid range for water. One example is 1-ethyl-3-methylimidazolium chloride-aluminum chloride, which is abbreviated as (emim)Cl—$AlCl_3$. This ionic liquid is liquid from about −100° C. to about 200° C. depending on the amount of (emim)Cl and $AlCl_3$. When the molar percentage of $AlCl_3$ is 65%, the melting point is −96° C.

The cation in the ionic liquid is an organic cation such as (emim)$^+$ while the anions are inorganic anions such as the anions of $AlCl_3$ ($AlCl_4^-$, $Cl^-$, $Al_2Cl_7^-$). The organic cations account for the low melting points, while the chemical properties are determined mostly by the anions. Finally, depending on the relative amounts of the inorganic anions, the ionic liquid can be basic, neutral or acidic. A review of ionic liquids can be found in Chemical and Engineering News, Mar. 30, 1998, pp. 32–37 and K. R. Seddon, "Ionic Liquids for Clean Technology: An Update," Molten Salt Forum Vols. 5–6 (1998) pp. 53–62, Trans Tech Publications, Switzerland.

WO 95/21806 discloses the alkylation of aromatics by an olefin using an ionic liquid as the catalyst. Specifically, the alkylation of benzene with ethylene using a (emim)Cl—$AlCl_3$ ionic liquid catalyst with 67 wt. % $AlCl_3$ and 33 wt. % (emim)Cl. U.S. Pat. No. 4,554,383 discloses a process to prepare p-tolualdehyde by reacting toluene and CO in the presence of a "melt" catalyst composed of a N-alkyl-pyridinium halide and aluminum chloride. WO 00/15594 discloses reacting an alkyl aromatic compound with CO in the presence of an acidic ionic liquid to form an alkyl aromatic aldehyde.

Although the carbonylation of aromatics (or olefins) is fairly facile, the carbonylation of saturated hydrocarbons is extremely difficult. The fundamental problem in the direct carbonylation of saturated hydrocarbons is the high stability of the C—C and C—H bonds. In view of the high stability of these bonds, attempts to directly convert saturated hydrocarbons to hetero organic molecules have met with few successes. For example U.S. Pat. No. 2,874,186 discloses a process for reacting carbon monoxide with normal paraffins, isoparaffins and naphthenes to produce ketones, acids and esters. The process involves placing the isoparaffin in a reactor with hydrogen fluoride and boron trifluoride (HF/$BF_3$) and carbon monoxide under high pressures. The products, which were obtained from this process, were ketones and carboxylic acids. U.S. Pat. No. 2,346,701 discloses preparing organic oxygen-containing compounds such as ketones and acids by reacting propane with carbon monoxide using an anhydrous aluminum halide catalyst, e.g., aluminum chloride. U.S. Pat. No. 3,356,720 discloses preparing oxygenated organic compounds by reacting saturated hydrocarbons with carbon monoxide using a Freidel-Crafts catalyst and a tertiary alkyl, phenyl alkyl or phenyl carbonyl halide. Both ketones and carboxylic acids are produced. It is also disclosed in WO 98/50336 that branched aliphatic hydrocarbons can be converted to branched aliphatic ketones by reacting the hydrocarbons with carbon monoxide at high pressures and super acidic conditions. The super acidic conditions are produced by the combination of a protic acid such as HF and a Lewis acid such as $BF_3$. The reaction is carried out at temperatures of about 0° C. to about 35° C. and pressures of about 10 to 200 atmospheres.

All of the above references disclose the use of superacids, for carbonylation, which are corrosive, volatile and environmentally harmful. In the pursuit of an environmentally green process for the carbonylation of saturated hydrocarbons, applicants have developed a process using ionic liquids. The process involves reacting the hydrocarbon with carbon monoxide in the presence of an acidic ionic liquid to produce an oxygenated saturated hydrocarbon. The ionic liquid serves both as the catalyst and the solvent. One example of an ionic liquid is $AlCl_3$ (n-butylpyridinium chloride) with a ratio of $AlCl_3$:(n-butylpyridinium chloride) of 64:36 by weight.

SUMMARY OF THE INVENTION

As stated, this invention relates to a process for preparing an oxygenated saturated hydrocarbon comprising contacting a saturated hydrocarbon with carbon monoxide and an acidic ionic liquid catalyst at reaction conditions to provide an oxygenated saturated hydrocarbon.

Another embodiment of the invention involves hydrogenating the oxygenated saturated hydrocarbon to give a reduced oxygenated saturated hydrocarbon.

In a specific embodiment isobutane is reacted with CO in the presence of $AlCl_3$ (n-butylpyridinium) ionic liquid to give methyl isopropyl ketone.

These and other objects and embodiments will become clearer after a detailed description of the invention.

DETAILED DESCRIPTION OF THE INVENTION

Generally, the present invention relates to the direct carbonylation of saturated hydrocarbons to form the corresponding oxygenated saturated hydrocarbons. By oxygenate is meant an oxygen containing saturated hydrocarbon, with saturated referring to the hydrocarbon portion of the molecule. Non-limiting examples of these oxygenates are ketones, aldehydes and acids. Without wishing to be bound by any particular theory, the reaction pathway by which direct carbonylation to ketones takes place involves the formation of a carbocation species, i.e., a carbenium or carbonium ion which is then reacted, i.e., intercepted, by carbon monoxide molecules forming a relatively stable oxycarbocation. The oxycarbocation undergoes further molecular rearrangement involving an intramolecular hydrogen transfer, i.e., hydride shift, to produce an aldehyde, and an intramolecular methyl shift to convert the aldehyde to the more stable ketone.

Accordingly, those saturated hydrocarbon compounds, which can be used in the present invention, are any of those that can form a carbocation at reaction conditions. The hydrocarbons, which meet these criteria, are any of those which contain at least one of a primary, secondary or tertiary carbon as described in standard organic chemistry texts. Preferred hydrocarbons are those which contain one or more tertiary carbon. For the purpose of this invention, the hydrocarbons which meet these criteria are the saturated hydrocarbons which include alkanes and cyclic alkanes. Although the number of carbon atoms which the saturated hydrocarbons can have is not a critical aspect of this invention, for practical purposes those having 1 to 30 carbon atoms are usually used and thus are preferred.

Included in the general category of alkanes are cyclic alkanes, straight chain alkanes, single and multiple branched alkanes. Cyclic alkanes include cyclic alkanes having one or more alkyl groups attached to the ring. Especially preferred alkanes are the branched alkanes (branched such that they contain one or more tertiary carbon) having from 4 to about 30 carbon atoms. Specific examples of branched alkanes include, but are not limited to, isobutane, isooctane, methylcyclopentane, methylcyclohexane, 2,3-dimethylbutane and 2-methyl-undecane. Further, mixtures of any of the $C_4$–$C_{30}$ alkanes can be used in the process and indeed mixtures can lead to very useful products. Examples of these mixtures include, but are not limited to, mixtures of butane and isobutane; mixtures of $C_6$ isomers including 2,2-dimethyl butane, 2,3 dimethyl butane, 2-methyl pentane, 3-methyl pentane and n-hexanes; detergent range isoparaffins which usually include $C_{10}$ to $C_{16}$ isoparaffins; etc. It should be pointed out that the initial hydrocarbon feed, in the presence of the ionic liquid catalyst at reaction conditions, can undergo isomerization from unbranched to branched (tertiary carbon) hydrocarbons. Thus, the preferred branched hydrocarbons can be generated in situ.

An ionic liquid, which serves as both catalyst and solvent, is required in order for the saturated hydrocarbon to react with the carbon monoxide. As stated, ionic liquids comprise an organic cation and an inorganic anion, and are represented by the general formula aA:(1-a)BX where "A" is a Lewis or Bronsted acid "a" has a value from about 0.55 to about 0.95, "B" is a quaternary nitrogen-containing cation and "X" is an anion which balances the charge on "B". Since "A" is always present in an excess amount, the ionic liquid will be acidic.

The anion of the ionic liquid is generally derived from the Lewis or Bronsted acid "A". Non-limiting examples of Lewis acids are halides of aluminum, boron, gallium, antimony, tantalum while examples of Bronstead acids are triflic acid, sulfuric acid, phosphoric acid, etc. Typically, the quaternary nitrogen-containing cation is an alkyl pyridinium or a dialkyl imidazolium cation. The alkyl group can be any alkyl group having from 1 to 18 carbon atoms and preferably 1 to 10 carbon atoms. The source of these cations are salts where the counterion, "X", can be a halide, triflate, sulfate, hydrosulfate or $PF_6^-$. Of the salts, the halides are preferred and of the halides the chlorides are especially preferred. Specific salts include but are not limited to 1-ethyl-3-methyl-imidazolium chloride, 4-butyl-2-methyl-imidazolium chloride, 1-butyl-3-ethyl-imidazolium chloride, 1-butyl-3-methyl-imidazolium bromide, 1-hexyl-3-methyl-imidazolium chloride, ethyl-pyridinium bromide, ethyl-pyridinium chloride, n-butyl-pyridinium chloride.

These quaternary nitrogen-containing compounds can be formed by means well known in the art and/or are commercially available. For example, 1-ethyl-3-methyl-imidazolium chloride can be prepared by boiling methylimidazole with ethylchloride. Similarly, n-butylpyridinium chloride can be prepared from pyridine and butylchloride.

The ionic liquids can be prepared by means well known in the art such as described in T. Welton, *Chemical Reviews,* 99, 8, 2071–2084 (1999). One technique is an acid-base neutralization reaction. For example, mixing equimolar amounts of n-butylpyridinium chloride with $AlCl_3$ results in a liquid of n-butylpyridinium$^+$—$AlCl_4^-$. If excess amounts of acid are present, then the ionic liquids will be acidic.

The carbonylation reaction is conducted by contacting the desired saturated hydrocarbon feed and carbon monoxide with the acidic ionic liquid catalyst. The three components can be mixed in any order although not necessarily with equivalent results. The process can be carried out in either a batch process or a continuous flow process. In a batch process one way of carrying out the process involves placing the ionic liquid in an autoclave followed by the addition of or simultaneous addition of the desired hydrocarbon and finally, pressuring with carbon monoxide. Of course the reverse addition can also be done, i.e., carbon monoxide first and then hydrocarbon. The ionic liquid also acts as the solvent. The pressure of carbon monoxide can vary considerably but usually, is between 345 kPa to about 27,580 kPa (50 to 4,000 psig). Generally, the ratio of ionic liquid to hydrocarbon ranges from about 0.1:1 to about 50:1 and preferably from about 5:1 to about 20:1. The carbon monoxide can be either pure CO or a CO containing gas. The presence of $CO_2$ or $H_2$ in a CO gas mixture generally does not affect the carbonylation reaction. Therefore, synthesis gas which contains CO, $H_2$ and some $CO_2$ can be used in the current process. The mole ratio of CO to hydrocarbon can vary considerably but is usually from about 1:1 to about 50:1. The autoclave is then heated to a temperature of about 20° C. to about 200° C. and preferably from about 50° C. to about 150° C. for a time sufficient to form the desired oxygenated hydrocarbon. The time varies from about 1 min. to about 20 hrs. After the desired time has elapsed, the autoclave is vented.

After the reaction has been stopped, the product oxygenates will usually be present as a complex with the acid and must be separated. Any separation process well known in the art can be used including solvent extraction, supercritical extraction or volatilization. The term volatilization includes evaporation, vaporization, flash distillation and combinations thereof.

After having separated the oxygenated product from the product mixture, the oxygenated product can be hydrogenated, i.e., the oxygenated part, in a separate step. Hydrogenation is carried out by reacting the oxygenated hydrocarbon with a hydrogen containing gas in the presence of a hydrogenation catalyst to give the corresponding reduced oxygenated hydrocarbon. Again, the process can be carried out in a batch or continuous mode with continuous mode being preferred. Hydrogenation conditions include a temperature of about 20° C. to about 200° C., a pressure of about 345 kPa to about 27,580 kPa (50 to about 4,000 psig) and a liquid hourly space velocity of about 0.5 to about 10 $hr^{-1}$. In a batch mode the contact time varies from about 1 minute to about 5 hrs.

The hydrogenation catalyst comprises a hydrogenation component dispersed on a suitable support. Hydrogenation catalyst components include but are not limited to Group VIII metals of the Periodic Table, molybdenum, tungsten and mixtures thereof. Preferred hydrogenation components are the platinum group metals. The platinum group metals are platinum, palladium, rhodium, iridium, ruthenium and osmium. Preferred platinum group metals are platinum and palladium. The hydrogenation catalyst component is present in an amount from about 1 to about 10 wt. % of the catalyst as the metal. The support can be any support, which is inert to the reactants and products and has a sufficient surface area in order to disperse the hydrogenation component thereon. The surface area should be at least 5 m$^2$/g. Specific examples include, but are not limited to, metal oxides, aluminas, silica, molecular sieves, organic polymers, halogenated metal oxides, carbon, fluorinated carbon, etc. These hydrogenation catalysts are prepared by conventional techniques in which one or more hydrogenation metal compounds are dissolved in a suitable solvent and then contacted with the support. Contacting can be done by impregnation, spray drying, etc. As stated above, the final form of the hydrogenation component can be a metal, metal oxide or a metal compound. Finally, the concentration of the hydrogenation component can vary from about 1 to about 10 wt. % of the catalyst as the metal. A specific example is palladium dispersed on carbon.

Alternatively, by adding a hydrogenation component to the acidic ionic liquid and using a CO and $H_2$ mixture, reductive carbonylation can be carried out in one step. The hydrogenation components are the same as those enumerated above.

The volume ratio of $CO/H_2$ can vary considerably but usually is from about 1:1 to about 10:1. Further, the volume ratio of $H_2$ to oxygenated hydrocarbon varies from about 1 to about 10. The carbon monoxide and hydrogen can be introduced separately, premixed and introduced as one gas or snygas can be used. It should be pointed out that for $C_1$ to $C_3$ hydrocarbons, i.e., methane, ethane and propane, although carbonylation can be carried out (see example 11) reductive carbonylation is preferred in order to drive the carbonylation reaction. In this case one obtains reduced oxygenated saturated hydrocarbons which are mostly alcohols.

The oxygenated (or reduced oxygenated) hydrocarbons of this invention have various uses as solvents, gasoline additives, surfactants, monomers for polymers, etc.

The following examples are set forth to illustrate the invention. It is to be understood that the examples are only by way of illustration and are not intended as an undue limitation on the broad scope of the invention as set forth in the appended claims.

EXAMPLE 1

In a dry box, 32.2 g $AlCl_3$ and 17.8 g n-butylpyridinium chloride were mixed and then transferred to an autoclave equipped with a stirrer and pressure gauge. To this there were added 28.0 g of isobutane and the reactor was pressurized to 1250 psig with CO at $-17°$ C. and then warmed up to room temperature (pressure increased to 1450 psig). The reactor was heated to 60° C. for 2.5 hours and analysis showed 2.7% conversion with 100% selectivity to methyl-isopropylketone.

EXAMPLE 2 TO 13

Using the basic procedure set forth in Example 1 various experiments were carried out using different combinations of catalysts and conditions. These results are presented in Table 1 below.

The following abbreviations will be used in Table 1.

| | | |
|---|---|---|
| NBPC | = | n-butylpyridinium chloride |
| BMIM | = | 4-butyl-2-methylimidazolium choride |
| BMIM*PF6 | = | 4-butyl-2-methylimidazolium chloride phosphorus hexafluoride |
| $iC_4$ | = | Isobutane |
| MCP | = | Methylcyclopentane |
| MCH | = | Methylcyclohexane |
| 2,5 DMH | = | 2,5 dimethylhexane |
| MIPK | = | Methyl-isopropylketone |

TABLE 1

EFFECT OF IONIC LIQUID ON CARBONYLATION ACTIVITY

| Ex. # | Ionic Component #1 (wt. in g) | Ionic Component #2 (wt. In g) | Hydro-carbon (wt.) | Temp (° C.) | Reaction Time (Hr.) | Conversion (%) | Selectivity To MIPA (%) |
|---|---|---|---|---|---|---|---|
| 2 | NBPC (17.8) | $AlCl_3$ (32.2) | $iC_4$ (34 g) | 100 | 5 | 3.3 | 97 |
| 3 | NBPC (17.9) | $^1AlCl_3$ (32.2) | $iC_4$ (33 g) | 100 | 4 | 6.5 | 93 |
| 4 | NBPC (17.8) | $^2AlCl_3$ (32.2) | $iC_4$ (35.4 g) | 100 | 4 | 8.0 | 91 |
| 5 | NBPC (17.8) | $AlBr_3$ (64.4) | $iC_4$ (34.6 g) | 134 | 6 | 17.0 | 0 |
| 6 | $TaCl_5$ (86.5) | $AlCl_3$ (32.2) | $iC_4$ (35.0 g) | 100 | 1.5 | 1.0 | 94 |
| 7 | BMIM (20.9) | $AlCl_3$ (32.2) | $iC_4$ (37.5 g) | 100 | 3 | 3.6 | 90 |
| 8 | NBPC (17.8) | $AlCl_3$ (32.2) | MCP (40.0 g) | 100 | 1 | 56.0 | —[5] |
| 9 | NBPC (17.8) | $AlCl_3$ (32.2) | MCH (47.0 g) | 100 | [4]— | 72.0 | —[6] |
| 10 | NBPC (17.8) | $AlBr_3$ (64.4) | MCP (40.0 g) | 100 | 5 | 93.4 | —[5] |
| 11 | NBPC (17.8) | $AlCl_3$ (32.2) | $^3$Raffinate (40.8 g) | 100 | 1.75 | N/A | —[5] |
| 12 | NBPC (13.35) | $AlCl_3$ (24.15) | 2,5 DMH (48.75 g) | 100 | 4 | 56.7 | 0[6] |
| 13 | BMIM*PF$_6$ (50.0) | $H_2SO_4$ (5.0) | $iC_4$ (34.4 g) | 100 | 4 | 0 | — |

[1]Also contained 0.02 mole HCl
[2]Also contained 0.04 mole HCl
[3]Paraffinic (non-normal) Naphtenic Liquid Hydrocarbon Mixture with a 193–259° C. Boiling Range
[4]Heated to 100° C. and then cooled to room temperature
[5]Oxygenated Compounds present in product
[6]No Oxygenated Compounds observed

We claim as our invention:

1. A process for preparing an oxygenated saturated hydrocarbon comprising contacting a saturated hydrocarbon with a gas comprising carbon monoxide and an acidic ionic liquid catalyst at reaction conditions to provide an oxygenated saturated hydrocarbon, where the acidic ionic liquid catalyst comprises an organic cation and an inorganic anion having an empirical formula of aA:(1−a)BX where "A" is a Lewis or Bronsted acid, "a" has a value of about 0.55 to about 0.95, "B" is a quarternary nitrogen-containing cation and "X" is an anion which balances the charge on "B".

2. The process of claim 1 where the saturated hydrocarbon is at least one saturated hydrocarbon having from 1 to 30 carbon atoms.

3. The process of claim 2 where the saturated hydrocarbon is selected from the group consisting of alkanes, cycloalkanes and mixtures thereof.

4. The process of claim 3 where the alkanes are branched alkanes which contain at least one tertiary carbon.

5. The process of claim 4 where the alkanes are selected from the group consisting of isobutane, isooctane, 2,3-dimethylbutane, 2,2-dimethylbutane, 2-methylpentane, 3-methyl pentane, $C_{10}$ to $C_{16}$ isoparaffins and mixtures thereof.

6. The process of claim 1 where the saturated hydrocarbon contains at least two tertiary carbons which provide an oxygenated saturated hydrocarbon containing at least two oxygenated carbons.

7. The process of claim 1 where the oxygenated hydrocarbon is a ketone.

8. The process of claim 1 where the process is carried out in a batch mode and the reaction conditions include a pressure of about 689 to about 20670 kPa (100 to about 3000 psig), a temperature of about 0° C. to about 200° C. and a contact time of about 5 min to about 24 hours.

9. The process of claim 1 where the process is carried out in a continuous mode and the reaction conditions include a pressure of about 689 to about 20670 kPa (100 to about 3000 psig), a temperature of about 0° C. to about 200° C., and a space velocity of about 0.5 to about 10 $hr^{-1}$.

10. The process of claim 1 where the Lewis acid is selected from the group consisting of halides of aluminum, boron, gallium, antimony, tantalum and mixtures thereof; and the Bronsted acid is selected from the group consisting of triflic acid, sulfuric acid, phosphoric acid and mixtures thereof.

11. The process of claim 1 where the quarternary nitrogen-containing cation is selected from the group consisting of alkyl pyridinium and di-alkyl imidazolium cations and the anion "X" is selected from the group consisting of halide, triflate, sulfate hydrosulfate and $PF_6^-$.

12. The process of claim 1 where the ionic liquid is selected from the group consisting of n-butylpyridinium chloride-aluminum chloride, 4-butyl-2-methyl-imidazolium chloride-aluminum chloride, 4-butyl-2-methyl-imidazolium chloride phosphorus hexafluoride-aluminum chloride.

13. The process of claim 1 where the ionic liquid to hydrocarbon weight ratio varies from about 0.1:1 to about 50:1.

14. The process of claim 13 where the mole ratio of CO to hydrocarbon varies from about 1:1 to about 50:1.

15. The process of claim 1 further comprising contacting the oxygenated saturated hydrocarbon with hydrogen and a hydrogenation catalyst at hydrogenation conditions to convert the oxygenated saturated hydrocarbon to a reduced oxygenated saturated hydrocarbon.

16. The process of claim 15 where the hydrogenation is carried out in a continuous mode and the hydrogenation conditions include a $H_2$/oxygenated hydrocarbon volume ratio of about 1 to about 10, a pressure of about 345 to about 27,580 kPa, a temperature of about 20° C. to about 200° C. and a liquid hourly space velocity of about 0.5 to about 10/$hr^{-1}$.

17. The process of claim 15 where the hydrogenation catalyst comprises a hydrogenation component selected from the group consisting of a Group VIII metal component, a tungsten component, a molybdenum component and mixtures thereof dispersed on a support.

18. The process of claim 17 where the hydrogenation catalyst comprises palladium on carbon.

19. The process of claim 1 further comprising separating the oxygenated saturated hydrocarbons from the ionic liquid by selective volatilization, solvent extraction or supercritical extraction.

20. The process of claim 1 where a hydrogenation catalyst is present with the ionic liquid catalyst and the gas comprises hydrogen and carbon monoxide.

21. The process of claim 20 where the hydrogenation catalyst comprises a Group VIII compound, a tungsten compound, a molybdenum compound and mixtures thereof.

22. The process of claim 20 where the hydrogenation catalyst comprises a Group VIII component, a tungsten component, a molybdenum component and mixtures thereof dispersed on a support.

23. The process of claim 20 where the volume ratio of $CO/H_2$ varies from about 1:1 to about 1:10.

* * * * *